United States Patent [19]

Neustadt et al.

[11] Patent Number: 4,778,795
[45] Date of Patent: Oct. 18, 1988

[54] CARBOXYALKYL DIPEPTIDES AS ANTIGLAUCOMA AGENTS

[75] Inventors: Bernard R. Neustadt, West Orange; David R. Andrews, Bloomfield; Paul E. McNamara, Scotch Plains; Robert W. Watkins, Great Meadows, all of N.J.

[73] Assignee: Schering Corporation, Kenilworth, N.J.

[21] Appl. No.: 903,545

[22] Filed: Sep. 3, 1986

Related U.S. Application Data

[60] Division of Ser. No. 797,104, Nov. 11, 1985, Pat. No. 4,616,012, which is a continuation-in-part of Ser. No. 555,311, Nov. 25, 1983, Pat. No. 4,559,340.

[51] Int. Cl.$^4$ .................. A61K 31/505; A61K 31/44
[52] U.S. Cl. .................................... 514/259; 514/288; 514/913
[58] Field of Search ................. 514/259, 913; 544/288

[56] References Cited

U.S. PATENT DOCUMENTS

| 3,539,564 | 11/1970 | Shetty | 544/288 |
|---|---|---|---|
| 3,549,629 | 12/1970 | Shetty | 544/288 |
| 3,549,636 | 12/1970 | Shetty | 544/288 |
| 3,816,631 | 6/1974 | Novello | 514/259 |
| 4,338,435 | 7/1982 | Haugwitz | 544/12 |
| 4,376,768 | 3/1983 | Ozaki et al. | 514/222 |
| 4,431,645 | 2/1984 | Smith et al. | 544/13 |
| 4,468,396 | 8/1984 | Magatti | 544/13 |
| 4,551,452 | 11/1985 | Marfat | 514/222 |

FOREIGN PATENT DOCUMENTS

| 56637 | 7/1982 | European Pat. Off. | 514/259 |
|---|---|---|---|
| 849362 | 6/1962 | United Kingdom | 514/288 |
| 980593 | 1/1965 | United Kingdom | 544/288 |
| 2057439 | 4/1981 | United Kingdom | 514/259 |

OTHER PUBLICATIONS 44,892/59—Jan. 8, 1959—Merck & Co.—Section 43 of Pat. Act. 1952-1955—Publication.
Abstract of E.P. Application 95584—Dec. 1983.
Abstract of Aust. Pat. Appl. 8,313,837, Nov. 1983.

Primary Examiner—Douglas W. Robinson
Attorney, Agent, or Firm—Richard C. Billups; James R. Nelson; Stephen I. Miller

[57] ABSTRACT

Methods and pharmaceutical compositions are disclosed for reducing intraocular pressure. The methods and compositions employ an active ingredient which comprises certain benzothiadiazinyl and quinazolinyl substituted carboxyalkyl dipeptides wherein the benzothiadiazinyl or quinazolinyl portions are joined to the dipeptide portions by an aminocarbonyl group.

18 Claims, No Drawings

CARBOXYALKYL DIPEPTIDES AS ANTIGLAUCOMA AGENTS

This application is a divisional of Ser. No. 797,104 filed Nov. 11, 1985, now U.S. Pat. No. 4,616,012, which is a continuation in part of Ser. No. 555,311, filed Nov. 25, 1983, now U.S. Pat. No. 4,559,340.

The present invention relates to ophthalmic pharmaceutical compositions comprising benzothiadiazinyl and quinazolinyl substituted carboxyalkyl dipeptides, wherein the benzothiadiazinyl or quinazolinyl portions are joined to the dipeptide portions by an aminocarbonyl group, and to methods for using said compositions in the treatment of elevated intraocular pressure, especially that associated with glaucoma.

BACKGROUND OF THE INVENTION

Glaucoma is an ocular disease complex associated with an elevated pressure within the eye (i.e., intraocular pressure, IOP). As a result of the elevated IOP, damage to the optic nerve resulting in irreversible loss of visual function may ensue. Untreated, this condition may eventually lead to blindness.

Ocular hypertension, i.e., a condition of elevated intraocular pressure without optic nerve damage or characteristic glaucomatous visual field loss, is now believed by the majority of ophthalmologists to represent the earliest phase in the onset of glaucoma.

A number of the drugs presently employed to treat glaucoma are not entirely satisfactory, particularly in the earliest course of the disease when the side effects they produce are often worse than the symptoms of the disease.

Epinephrine, used as a topical solution, must be utilized cautiously in patients with high blood pressure, diabetes, hyperthyroidism and cerebral arteriosclerosis due to the possibility of systemic action.

Timolol, a clinically utilized, topically applied agent for lowering IOP, must be used with caution in patients in whom beta-adrenergic blockage may be undesirable. Systemic absorption of topically administered timolol and the resulting systemic beta-blockage are responsible for the contraindication of timolol therapy in glaucoma patients with compromised pulmonary function and in patients who cannot tolerate its systemic cardiovascular actions.

Pilocarpine, a topical drug, although considered systemically harmless and quite effective, may cause considerable local difficulties. Pupil constriction causes the eye to lose its ability to adapt from light to dark. Accommodation may become so stimulated that the patient's refraction is sometimes incorrect and vision becomes blurred. The drug itself may cause a local vasodilation and red eyes. Irritation is common.

Carbonic anhydrase inhibitors have been used systemically but they have a number of disadvantages. While effective in lowering intraocular pressure, they often cause a numbness and tingling, gastrointestinal upsets and, frequently, depression, lethargy, a loss of appetite, and general malaise. European Patent Application No. 81400326.5, Publication No. 36,351, attempts to overcome these difficulties by the topical administration of an alkali metal salt of a carbonic anhydrase inhibitor.

The present invention provides a new method for reducing and controlling elevated IOP, especially the elevated IOP associated with glaucoma.

SUMMARY OF THE INVENTION

The invention sought to be patented in its pharmaceutical composition aspect is a topical ophthalmologically acceptable composition useful for reducing and controlling elevated intraocular pressure, especially elevated IOP associated with glaucoma, which comprises an intraocular pressure reducing effective amount of a compound of the formulae:

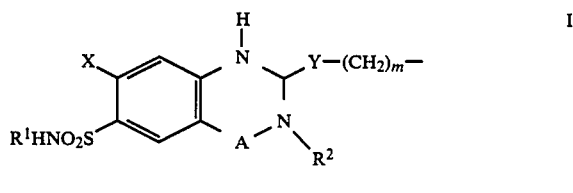

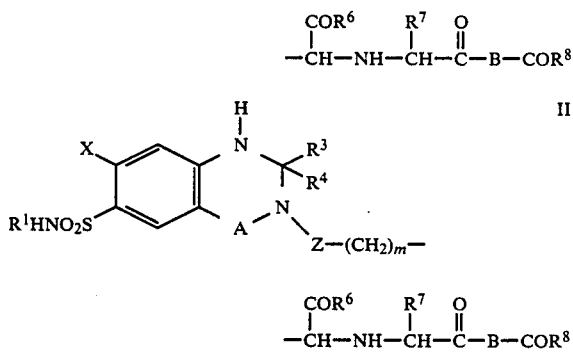

or their isomers or pharmaceutically acceptable salts thereof, wherein

A is —SO$_2$— or

X is Cl or CF$_3$;

Y is

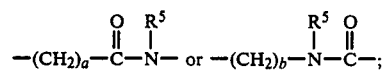

Z is

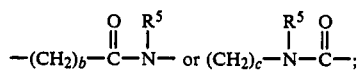

B is

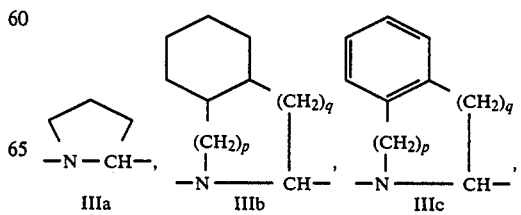

-continued

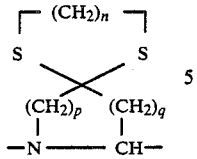
IIId

R[1] is hydrogen or lower alkyl;
R[2] and R[5] are independently hydrogen, lower alkyl, phenyl, or phenyl(lower)alkyl;
R[3] and R[4] are independently hydrogen, lower alkyl, haloloweralkyl, phenyl, or phenyl(lower)alkyl, or R[3] and R[4] taken together with the carbon to which they are attached can form a 5-7 membered cycloalkyl ring;
R[6] and R[8] are independently hydroxy, alkoxy having from 1 to 8 carbon atoms, L—$Q_r$—$(CH_2)_s$—O—, wherein L is phenyl, substituted phenyl, 1-naphthyl or 2-naphthyl; Q is oxygen or sulfur; r is 0 or 1 and s is 0 to 4; and wherein the substituents on the phenyl are chosen from group M, wherein M is halogen, hydroxy, trifluoromethyl, alkoxy having from 1 to 6 carbon atoms, alkyl from 1 to 6 carbon atoms, 2-furanyl, 3-furanyl, 2-thienyl, 3-thienyl and phenyl (which phenyl group may be substituted with halogen, hydroxy, trifluoromethyl, alkoxy having from 1 to 6 carbon atoms or alkyl having from 1 to 6 carbon atoms); provided that when s is zero, r is zero; —OCH$_2$—OCO-alkyl wherein the alkyl has from 3 to 8 carbon atoms, —OCH$_2$CO-phenyl, wherein the phenyl may be substituted with group M, 1-glyceryl,

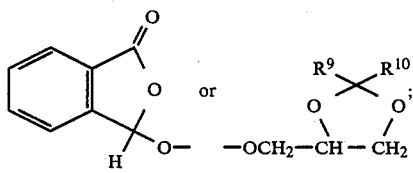

R[7] is hydrogen, lower alkyl, or aminoloweralkyl;
R[9] is hydrogen, lower alkyl, unsubstituted or substituted phenyl, and substituted or unsubstituted phenyl lower alkyl, wherein phenyl may be substituted by group M;
R[10] is hydrogen or lower alkyl;
a is 0-8;
b is 1-8;
c is 2-8;
m is 1-4;
n is 0 or 1;
p and q are each 0, 1 or 2, provided that in formulae IIIb and IIIc the sum of p and q is 1 or 2, and that in formula IIId, p is not 0; in combination with an ophthalmologically acceptable carrier for topical use.
The compounds useful in this pharmaceutical compositions include those disclosed in Ser. No. 555,311, filed Nov. 25, 1983.
When B is formula IIIb or IIIc, the preferred sum of p and Q is 1; when B is of formula IIId, preferred values for each of p and q are 1.
For compounds of formula I wherein Y is

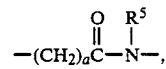

preferred compounds are those wherein m is 3 or 4. For compounds of formula I wherein Y is

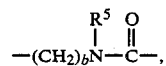

preferred compounds are those wherein m is 1 or 2. Also preferred are compounds wherein R[7] is hydrogen, methyl or aminobutyl, compounds wherein R[1] and R[2] are hydrogen or methyl, compounds wherein X is chlorine, and compounds wherein R[6] is hydroxy, ethoxy, methoxy, phenoxyethoxy, pivaloyloxymethoxy, or

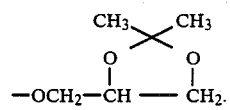

Especially preferred are compounds wherein both R[6] and R[8] are hydroxy.

The invention sought to be patented in its pharmaceutical method aspect is a method for reducing and controlling elevated intraocular pressure, especially that associated with glaucoma, in a mammal such as man, which method comprises administering to said mammal an effective amount of the above-defined pharmaceutical composition. The method can also employ a beta adrenergic blocking agent or an anti-inflammatory steroid in combination with the composition of the invention.

DETAILED DESCRIPTION OF THE INVENTION

The compounds of formulae I and II above can be prepared by the methods disclosed in co-pending U.S. application Ser. No. 555,311, filed Nov. 25, 1983. The disclosure of which is incorporated herein by reference for that purpose.

As used herein, "lower alkyl" means straight or branched chain hydrocarbon radicals of from 1 to 6 carbons, e.g. methyl, ethyl, propyl, isopropyl, butyl, t-butyl, pentyl and hexyl. Similarly, "lower alkoxy" means straight or branched alkoxy radicals having 1 to 6 carbon atoms, e.g. methoxy, ethoxy, propoxy, butoxy, iso-butoxy, pentoxy and hexyloxy. "Halogen" means fluorine, chlorine and bromine.

Compounds employed in the instant invention include various stereoisomers and the invention contemplates all such isomers in pure form and admixture. Preferred stereoisomers are those in which the absolute configuration at each of the three carbon atoms adjacent to both a nitrogen and a carboxyl group corresponds most closely to the absolute configuration of L-amino acids.

Examples of suitable compounds for use in the present invention are as follows:
1-{N-[1(S)-ethoxycarbonyl-5-[2-(6-chloro-3,4-dihydro-1,1-dioxo-7-sulfamoyl-1,2,4-benzothiadiazin-3-yl)acetamido]-pentyl]-(S)-alanyl}-cis,syn-octahydroindole-2(S)-carboxylic acid, 1-{N-[1(S)-carboxy-5[2-(6-chloro-3,4dihydro-1,1-diox-o-7-sulfamoyl-1,2,4-benzothiadiazin-3-yl)acetamido]-pentyl]-(S)-alanyl}-cis,syn-octahydroindole-2(S)-carboxylic acid, 1-{N-[1(S)-ethoxycarbonyl-4-[2-(6-chloro-3,4-dihydro-1,1-dioxo-7-sulfamoyl-1,2,4-benzothiadiazin-3-yl)acetamido]-butyl]-(S)-alanyl}-cis,syn-octahydroindole-2(S)-carboxylic acid, 1-{N-[1(S)-carboxy-4-[2-(6-chloro-3,4-dihydro-1,1-dioxo-7-sulfamoyl-1,2,4-benzothiadiazin-3-yl)acetamido]-butyl]-(S)-alanyl}-cis,syn-octahydroindole-2(S)-carboxylic acid, 1-{N-[1(S)-ethoxycarbonyl-2-(N-(6-chloro-3,4-dihydro-1,1-dioxo-7-sulfamoyl-1,2,4-benzothiadiazin-3-yl-methyl)carbamoyl)ethyl]-(S)-alanyl}-cis,syn-octahydroindole-2(S)-carboxylic acid, 1-{N-[1(S)-carboxy-2-(N-(6-chloro-3,4-dihydro-1,1-dioxo-7-sulfamoyl-1,2,4-benzothiadiazin-3-yl-methyl)carbamoyl)ethyl]-(S)-alanyl}-cis,syn-octahydroindole2(S)-carboxylic acid, 1-{N-[1(S)-ethoxycarbonyl-2-(N-(6-chloro-3,4-dihydro-1,1-dioxo-7-sulfamoyl-1,2,4-benzothiadiazin-2-yl-methyl)-carbamoyl)ethyl]-(S)-alanyl}-cis,synoctahydroindole-2(S)-carboxylic acid, 1-{N-[1(S)-ethoxycarbonyl-2(N-2-(6-chloro-3,4-dihydro-1,1-dioxo-7-sulfamoyl-1,2,4-benzothiadiazin-2-yl)ethyl)-carbamoyl)ethyl]-(S)-alanyl}-cis,synoctahydroindole-2(S)-carboxylic acid, 1-{N-[1(S)-carboxy-2-(N-2-(6-chloro-3,4-dihydro-1,1-dioxo-7-sulfamoyl-1,2,4-benzothiadiazin-2-yl-ethyl)-carbamoyl)-ethyl]-(S)-analyl}-cis,synoctahydroindole-2(S)-carboxylic acid, and 1-{N-[1(S)-carboxy-2(N-(6-chloro-3,4-dihydro-1,1-dioxo-7-sulfamoyl-1,2,4-benzthiadiazin-2-yl-methyl)-carbamoyl)-ethyl]-(S)-alanyl}-cis,syn-octahydroindole-2(S)-carboxylic acid, The compounds employed in this invention form salts with various inorganic and organic acids and bases which are also within the scope of this invention. Such salts include ammonium salts, alkali metal salts, e.g. sodium and potassium salts, and alkaline earth metal salts, e.g. calcium and magnesium salts. Salts with organic and inorganic acids may be prepared, e.g., HCl, HBr, H2SO4, H3PO4, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HCl and maleate) are preferred, especially the maleate.

The salts may be formed by conventional means, as by reacting the free acid or base forms of the product with one or more equivalents of the appropriate base or acid in a solvent or medium in which the salt is insoluble, or in a solvent such as water which is then removed in vacuo or by exchanging the cations of an existing salt for another cation on a suitable ion exchange resin.

Ocular hypertensive activity of the compounds of the invention may be tested by the procedure described by Watkins et al., J. Ocular Pharmacol. 1 (2): 161–168, 1985.

The compounds employed in the invention are administered in the form of ophthalmic pharmaceutical compositions adapted for topical administration to the eye; such as solutions, suspensions, ointments and solid inserts. Formulations of these compounds may contain from about 0.00001 to about 1.0%, preferably 0.00001 to 0.1%, and especially 0.00001 to 0.001% of medicament.

Other concentrations may be employed provided the dose is effective in lowering intraocular pressure. As a unit dosage form, between about 0.005 µg to about 0.5 mg, preferably 0.005 µg to 50 µg, and especially 0.005 µg to 0.5 µg of the active compound is applied to the human eye, generally on a daily basis. Individual dosage requirements are variable and must be administered by the attending clinician on the basis of the severity of the disease and the condition and response of the patient.

To prepare suitable dosage forms, the active compounds may be conveniently admixed with a non-toxic pharmaceutically acceptable carrier suitable for topcial ophthalmolgic administration. Typical of such pharmaceutically acceptable carriers are, for example, water, mixtures of water and water-miscible solvents such as lower alkanols or vegetable oils, petroleum based jelly, and including also from 0.5 to 5% by weight of hydroxyethyl cellulose, ethyl oleate, carboxymethyl cellulose, polyvinylpyrrolidone, and other water soluble ophthalmologically acceptable non-toxic polymer, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acid salts; ethlacrylates; polyacrylamides; natural products such as gelatin, alginates, pectins, tragacanth, karaya, chondrus, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, neutralized carbopol and xanthan gum; and mixtures of these polymers. The pharmaceutical preparation may also contain non-toxic auxiliary substances such as emulsifying, preserving, wetting, bodying agents and the like, as for example, polyethylene glycols 200, 300, 400 and 600; carbowaxes 1,000, 1,500, 4,000, 6,000 and 10,000; antibacterial components such as quaternary ammonium compounds; phenylmercuric salts known to have cold sterilizing properties and which are non-injurious in use; thimerosal; methyl and propyl paraben; benzyl alcohol; phenyl ethanol; buffering ingredients such as alkali metal chloride, borate, acetate, gluconate buffers; antioxidants such as sodium matabisulfite, butylated hydroxyanisole (BHA), butylated hydroxytoluene (BHT) and the like; and other conventional ingredients such as sorbitan monolaurate, triethanolamine oleate, polyoxyethylene sorbitan monopalmitylate, dioctyl alkali metal sulfosuccinate, monothioglycerol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts that are known in the art that are suitable for this use include those described in British Pat. No. 15611, and in U.S. Pat. Nos. 3,993,071; 3,986,510; 3,868,455; and 3,867,510. Solid water insoluble inserts, such as those prepared from ethylene vinyl acetate copolymer, may also be utilized.

The compositions of the invention may include therapeutically effective amounts of additional ophthamologically acceptable therapeutic agents in addition to the compounds of formulae I and II. For example, antibiotics and anesthetics, as well as other IOP-lowering agents may be present.

A particularly advantageous utility for the compounds of this invention lies in their use in pharmaceutical compositions which also contain other compounds known to be useful for the lowering of intraocular pressure. It is contemplated that pharmaceutical compositions containing compounds of this invention in conjunction with other IOP-lowering compounds will constitute a more effective and safer therapy than with compounds containing a single active compound. This effect is particularly advantageous when the compounds of this invention are used in combination with beta-adrenergic blockers. For purposes of the present invention, the term beta-adrenergic blocker means a compound which by binding to beta-adrenergic plasma membrane receptors reduces or eliminates sympathetic activity or blocks the effects of exogenously administered catecholamines or adrenergic drugs. See, for example, Weiner, N., Drugs that Inhibit Adrenergic Nerves and Block Adrenergic Receptors, in the Pharmaceutical Basis of Therapeutics (ed. A. G. Goodman, L. S. Goodman, A. Gilman), Mcmillan Publishing, New York, 1980, 6th ed., pp. 188-197. Examples of preferred beta-adrenergic blockers are atenolol (4-[2-hydroxy-3-[(1-methylethyl)amino]-propoxy]benzeneacetamide), metoprolol (1-[4-(2-methoxyethyl)phenoxy]-3-[(1-methylethyl)amino]-2-propanol), nadolol (5-[3[(1,1-dimethylethyl)amino]-2-hydroxypropoxy]-1,2,3,4-tetrahydro-2,3-naphthalenediol), pindolol (1-(1H-indol-4-yloxy)3-[(1-methylethyl)amino]-2-propanol), propranolol (1-[(1-methylethyl)amino]-3-(1-naphthalenyloxy)-2-propanol), thimolol (1-[(1,1-dimethylethyl)amino]-3-[(4-morpholinyl-1,2,5-thiadiazol-3-yl)oxy]-2-propanol), labetalol (2-hydroxy-5-[1-hydroxy2-[(1-methyl-3-phenylpropylmethoxy)ethyl]-phenoxy]-3-[(methylethyl)amino]-2-propanol), carteolol (5-[3-[(1,1-dimethylethyl)amino]-2-hydroxypropoxy]-3,4-dihydro-2(1H)-quinolinone), and dilevalol ([R-(R,R)]-2-hydroxy-5-[1-hydroxy-2-[(1-methyl-3-phenylpropyl)amino]ethyl]benzamide 4-methylbenzenesulfonate salt), and pharmaceutically acceptable salts and isomers thereof.

The usefulness of beta-adrenergic blockers for lowering intraocular pressure is known in the art. For example, the beta-adrenergic blocker timolol is currently approved by the U.S. Food and Drug Administration for topical intraocular use for the treatment of glaucoma. It is marketed in two dose strengths, i.e., 0.25% and 0.5%. As previously stated, this agent must be used with caution in a defined patient population becuase of recognized untoward side effects (see Physicians Desk Reference for Ophthalmology, 11th edition, 1983, p. 126, Medical Economics Co. Inc., Oradell, N.J. 07649).

As one aspect of the present invention, it is contemplated that a reduction in intraocular pressure equivalent to that obtained by use of a beta-blocker, e.g., the approved clinical dose of thimolol, may be obtained by use of a lower dose of beta-blocker when such lower dose is combined with an effective amount of a composition of this invention such as a composition including thimolol and 1-{N-[1(S)-carboxy-5[2-(6-chloro-3,4dihydro-1,1-dioxo-7-sulfamoyl-1,2,4-benzothiadiazin-3-yl)acetamido]-pentyl]-(S)-alanyl}-cis,syn-octahydroindole-2(S)-carboxylic acid, timolol and 1-{N-[1(S)-carboxy-2-(N-(6-chloro-3,4-dihyro-1,1-dioxo-7-sulfamoyl-1,2,4-benzothiadiazin-3-yl-methyl)carbamoyl)ethyl]-(S)-alanyl}cis,syn-octahydroindole-2(S)-carboxylic acid. It is anticipated that the use of the diminished dosage of beta-blocker will result in a reduction of severity and frequency of timolol-like related side effects.

For purposes of this treatment modality, the preferred ranges of the components of the composition of the invention are as follows:
beta-adrenergic blocker: 50μg to 250 μg
Compound of formula I or II: 0.025 μg to 5 μg For purposes of this invention the term "subthreshold intraocular pressure reducing concentration" of the IOP reducing compounds of this invention, e.g., 1-{N-[1(S)-carboxy-5[2-(6-chloro-3,4dihydro-1,1-dioxo-7-sulfamoyl-1,2,4-benzothiadiazin-3-yl)acetamido]-pentyl]-(S)-alanyl}-cis,syn-ocatahydroindole-2(S)-carboxylic acid or 1-{N-[1(S)-carboxy-2-(N-(6-chloro-3,4-dihyro-1,1-dioxo-7-sulfamoyl-1,2,4-benzothiadiazin-3-yl-methyl)carbamoyl)ethyl]-(S)-alanyl}-cis,syn-octahydroindole-2(S)-carboxylic acid, means an amount less than the threshold dose, i.e., one drop of 0.001% (w/v). Similarly for example, for purposes of the invention, the term "subthreshold intraocular pressure reducing concentration" of beta-adrenergic blocker, e.g. timolol, means an amount less than the threshold dose, i.e. one drop of 0.25% (w/v).

Those skilled in the art will appreciate that the "subthreaded intraocular pressure reducing concentration" will consist of a range of concentrations (doses), and that there will be a lower limit to said concentration below which the present invention will not operate. For purposes of this invention, this lower limit or minimum dosage may be considered to be about 5% of the effective dose (threshold dose) of the particular component. The subthreshold intraocular pressure reducing concentration that is actually utilized, whether for composition according to this invention or for a particular beta-adrenergic blocker will depend on, inter alia, the potency of each particular IOP reducing compound, the combination being administered and the age, size and condition of the patient being treated, as well as on the severity of the disease state.

Those skilled in the art will know that a particular dosage of active ingredient may be calculated if one assumes that one drop of solution is being administered and if one knows the concentration (w/v) of the particular solution that is being administered. Thus, one drop (1/20 ml) of a 0.25% solution (contains 2.5 mg of active per ml) is known to contain 0.125 mg or 125 μg of active.

It is also contemplated that a concentration of the inventive composition which is subthreshold for lowering IOP, when combined with a concentration of beta-adrenergic blocker which is also subthreshold for lowering IOP, will result in significant IOP-lowering. The clinical implication of such a result is that a combination of the two drugs will provide a clinically significant lowering of IOP with limited side effect liability, e.g., bradycardia and bronchoconstriction which occur with IOP-lowering effective concentrations of beta-adrenergic blockers.

For purposes of this treatment modality, the preferred ranges of the components of the composition of the invention are as follows:
beta-adrenergic blocker: from 5 μg to 125 μg
Compound of formula I or II: 0.005 μg to 1 μg Another advantageous clinical characteristic of this beta-blocker/compound of formula I or II combination is that the maximum lowering of IOP attainable from monotherapy with a beta-adrenergic blocker (e.g. timolol) can be significantly increased when combined with subthreshold concentrations of a compound of formula I or II. The clinical implication of these findings is that in patients whose elevated IOP (e.g. glaucoma) is not adequately controlled by maximum recommended concentrations of stranded therapy, e.g., timolol, that such patients could be treated with the combination of compounds to achieve greater lowering of IOP than that attainable by either treatment alone. Such treatment would result in greater clinical benefit with no increase in side effects.

For purposes of this treatment modality, the preferred ranges of the components of the composition of the invention are as follows:
beta-adrenergic blocker: from 25 µg to 500 µg
Compound of formula I or II: 0.005 µg to 1 µg The IOP-lowering effects of these combinations of the invention may be measured by the procedure described in the Watkins et al. article cited above.

The pharmaceutical compositions of the invention (compounds of formula I or II/beta-adrenergic blockers) are administered in the form of ophthalmic pharmaceutical compositions adapted for topical administration to the eye; such as solutions, suspensions, ointments and solid inserts. Formulations of the invention may contain the following amounts of each constituent:

Substituted carboxyalkyl dipeptides of formula I or II from 0.00001 to 0.1% (w/v) and especially 0.001 to 0.01% of medicament. As a unit dosage from, an amount of from between 0.005 µg to 50 µg, preferably 0.05 µg to 10 µg., and especially 0.5 µg to 5 µg of the active composition is applied to the human eye. Especially preferred are 1-{N-[1(S)-carboxy-5[2-(6-chloro-3,4dihydro-1,1-dioxo-7-sulfamoyl-1,2,4-benzothiadiazin-3-yl)acetamido]-pentyl]-(S)-alanyl}-cis,syn-octahydroindole-2(S)-carboxylic acid and 1-{N-[1(S)-ethoxycarbonyl-2-(N-(6-chloro-3,4-dihydro-1,1-dioxo-7-sulfamoyl-1,2,4-benzothiadiazin-3-yl-methyl)carbamoyl)ethyl]-(S)-alanyl}-cis,syn-octahydroindole-2(S)-carboxylic acid and 1-{N-[1(S)-carboxy-2-(N-(6-chloro-3,4-dihydro-1,1-dioxo-7-sulfamoyl-1,2,4-benzothiadiazin-3-yl-methyl)carbamoyl)ethyl]-(S)-alanyl}-cis,syn-octahydroindole-2(S)-carboxylic acid.

Beta-adrenergic blocker from 0.001 to 1% (w/v) and especially 0.01 to 0.5% to medicament. As a unit dosage form, an amount of beta-adrenergic blocker from between 0.5 µg to 500 µg and preferably 5 µg to 250 µg. of the active composition is applied to the human eye. Other concentrations may be employed provided the dose is effective in lowering intraocular pressure. Individual dosage requirements, i.e. the amount of each dose and the frequency of administration, will depend on the severity of the disease and the response of the patient.

In one embodiment of the method of the invention, it is anticipated that both active ingredients, i.e., compound of formula I or II and beta-blockers, will be administered simultaneously and be contained in one pharmaceutical dosage form. Each component being present in the dosage form in its own respective preferred concentration.

Suitable dosage forms for the pharmaceutical compositions comprising the substituted carboxyalkyl dipeptides and beta-adrenergic blockers may be conveniently admixed with compatible non-toxic pharmaceutically acceptable carriers suitable for topic ophthalmolgic administration such as those described supra.

We also contemplate that the elevation in IOP associated with the clinical ophthalmic and systemic use of anti-inflammatory steroids can be reduced by the administration of a composition of the present invention. In particular, an increase in IOP is most often associated with the ophthalmic administration of steroidal anti-inflammatory agents and may produce intractable glaucoma in some susceptible individuals. Anti-inflammatory steroids include, but are not limited to, hydrocortisone, cortisone, prednisolone, prednisone, dexamethasone, methylprednisolone, triamcinolone, betamethasone, alclometasone, flunisolide, beclomethasone, clorocortolone, diflorasone, halcinonide, fluocinonide, flucinolone, disoximetasone, medrysone, paramethasone, 9,21-dichloro-17-[(2-furanylcarbonyl)oxy]-11-hydroxy-16α-methyl-pregna-1,4-diene-3,20-dione and fluorometholone, and their pharmaceutically acceptable salts and esters. Preferred steroids and hydrocortisone, prednisolone, dexamethasone, betamethasone, beclomethasone, medrysone and fluoromethalone and their pharmaceutically acceptable salts and esters. This rise in IOP may occur with all modes of administration of the drugs, including systemic (usually oral), local injection (e.g., depot injection), and especially with ophthalmic topical or intravitreal administration. The composition of the invention may be administered following steroid treatment to lower elevated IOP, or may be co-administered with the steroid to suppress the IOP-raising effect of the steroid while not interfering with the anti-inflammatory activity of the steroid.

It is further contemplated that any possible combination of dosage forms may be used to administer the combination, e.g., oral steroid/topical composition of the invention, topical steroid/oral composition of the invention, oral steroid/oral composition of the invention, topical steroid/topical composition of the invention, and locally injected steroid/topical composition of the invention, although a preferred combination comprises a steroid and a topical composition of the invention. For ophthalmic use, a combination of a topical steroid and a topical composition of the invention is preferred. More preferred is a topical ophthalmic pharmaceutical dosage form comprising both a steroid and compound of formula I or II. Such compositions or combinations can be employed in a method for reducing and controlling the elevated IOP associated with ophthalmic and systemic use of steroidal anti-inflammatory agents, which method comprises administering to a mammal effective amounts of a steroid and a compound of formula I or II, either separately or in the same pharmaceutical composition.

Since the present invention relates to treatment with a combination of a composition of the invention and a sterodial anti-inflammatory agent wherein the composition of the invention and steroid may be administered separately, the invention also relates to combining separate pharmaceutical compositions in kit form, that is, combining two separate units, a composition of the invention including a compound of formula I or II and an anti-inflammatory steroid pharmaceutical composition, in a single package. Preferred components of the kit comprise a topical ophthalmological pharmaceutical composition containing a compound of formula I or II as defined above and a pharmaceutically acceptable anti-inflammatory steroid composition. More preferred components of the kit are a topical ophthamological pharmaceutical composition containing a compound of formula I or II and a topical ophthamological anti-inflammatory steroid pharmaceutical composition. A particular advantage of the more preferred embodiment of the kit resides in the ability to provide a combination of a composition of the invention which can be administered one or twice a day and a steroidal composition which may be administered as frequently as once each hour.

While the mechanism by which corticosteroids provide anti-inflammatory activity is unknown, their ability to provide relief from inflammatory symptoms is widely recognized. See, for example, Haynes, R. C., Jr., and Murad, F., "Adrenocorticotropic Hormone; Adrenocortical Steroids and Their Synthetic Analogs, Inhibitors of Andrenocortical Steroid Biosynthesis" in *The Pharmacological Basis of Theraputics* (ed., A. G. Gilman, L. S. Goodman, A. Gilman), Macmillan Publishing, New York, 1980, 6th ed., pp. 1470–1492, n.b. pg. 1490–1491.

In this combination treatment modality, topical formulations of the invention may combine the following amounts of each compound of formula I or II and steroidal constituent, or each constituent may be administered separately:

Compound of formula I or II: from about 0.00001 to about 1.0% (w/v) and especially about 0.0001 to about 0.01% of medicament. As a unit dosage form, an amount of a compound of formula I or II from between about 0.005 μg to about 500 μg, preferably about 0.005 μg to about 50 μg, and especially 0.005 μg of the active component is applied to the human eye. Individual dosage requirements, i.e., the amount of each dose and the frequency of administration, will depend on the particular potency of the compound selected the severity of the increase in IOP and the response of the patient.

Steroid from about 0.05 to about 1.5% (w/v) of medicament. As a unit dosage form, an amount of steroid from between 20 μg to 600 μg of the active composition is applied to the human eye. Individual dosage requirements, i.e., the amount of each dose and the frequency of administration will depend on the potency of the particular steroid, the severity of the disease and the response of the patient. Approximate ranges for such steroids are well known to those skilled in the art. The particular steroid employed will determine which compound of formula I or II and concentration thereof to select for use in a combination preparation.

In the preferred method of the invention, both active ingredients, i.e., compound of formula I or II and steroid, will be administered simultaneously and be contained in one pharmaceutical dosage form, each component being present in the dosage form in its own respective preferred concentration. When the steroid is administered systemically or topically other than in an ophthalmological composition, the concentration of the steroid in the composition and the unit dosage weight may vary considerably, depending as above on such factors as the potency of the steroid, its onset and duration of action as well as the severity of the disease, and the response of the patient. Appropriate dosage ranges for systemic and topical administration of each steroid arre well known in the art.

Those skilled in the art will know that for solutions and suspensions, a particular dosage of active ingredient may be calculated if one assumes that one drop of solution is being administered and if one known the concentration (w/v) of the particular solution that is being administered. Thus, one drop (1/20 ml) of a 0.25% solution (contains 2.5 mg of active per ml) is known to contain 0.125 mg or 125 μg of active.

Where utilized herein, the term "controlling the elevated intraocular pressure" means the regulation, attenuation and modulation of increased intraocular tension, e.g., the primary diagnostic symptom of the disease, glaucoma. The term also means that the diminution, in the otherwise elevated intraocular pressure, obtained by the practice of the invention is maintained for a significant period of time as, for example, between consecutive doses of the composition of the invention.

The following examples further illustrate the compositions of the invention and the preparation of compounds employed in the present invention.

EXAMPLE 1

1-{N-[1(S)-Ethoxycarbonyl-5-[2-(6-chloro-3,4-dihydro-1,1-dioxo-7-sulfamoyl-1,2,4-benzothiadiazin-3-yl)acetamido]pentyl]-(S)-alanyl}-cis,syn-octahydroindole-2(S)-carboxylic acid A. Combine 3-ethoxycarbonylmethyl-6-chloro-7-sulfamoyl-3,4-dihydro-1,2,4-benzothiadiazine-1,1-dioxide (7.7 g) with ethanol (EtOH) (250 ml) and 1N sodium hydroxide (NaOH) (70 ml) for 4 hours. Concentrate to 50 ml, add 1N hydrochloric acid (HCl) (70 ml), and extract with ethyl acetate (EtOAc). Dry the EtOAc extract over anhydrous magnesium sulfate and concentrate to obtain 3-carboxymethyl-6-chloro-7-sulfamoyl-3,4-dihydro-1,2,4-benzothiadiazine-1,1-dioxide.

B. Combine the product of part A (6.0 g), 6-amino-2-(1(S)-t-butyloxycarbonylethylamino)hexanoic acid ethylester (5.1 g), and N-hydroxy benzotriazole hydrate (2.6 g) with dry dimethylformamide (DMF) (150 ml) at 0° C. Add 1-(3-dimethylaminopropyl)-3-ethyl carbodiimide hydrochloride (DCI) (3.2 g). After 3 hours, concentrate the resultant solution and partition between EtOAc and 1N sodium bicarbonate (NaHCO3). Dry and concentrate the organic layer to obtain a crude oil (12.5 g), which can be further purified by chromatography on silica gel using chloroform:methanol:ammonia (90:9:1) to obtain N-5(S)-ethoxycarbonyl-5-[1(S)-(t-butyloxycarbonyl)ethylamino]pentyl-6-chloro-3,4-dihydro-1,1-dioxo-7-sulfamoyl-1,2,4-benzothiadiazine-3-acetamide.

C. Combine the product of step B (8.9 g) with HCl saturated dioxane (400 ml) for 24 hours. Decant the solution from the oil and dry the oil in vacuo to obtain N-(5(S)-ethoxycarbonyl-5-[1(S)-carboxyethylamino]-pentyl-6-chloro-3,4-dihydro-1,1-dioxo-7-sulfamoyl-1,2,4-benzothiadiazine-3-acetamide hydrochloride.

D. Combine the product of part C (5.8 g), triethylamine (1.8 g), 2(S)-benzyloxycarbonyl-(S),(S)-perhydroindole (2.4 g), and N-hydroxybenzotriazole.H2O (1.4 g) in dry dimethylformamide (100 ml) at 0° C., then add DCI (1.7 g). After 2 hours, concentrate and partition between EtOAc and 1N NaHCO3. Dry the organic layer and evaporate the solvent in vacuo. Chromatograph the resultant residue on silica gel, eluting with chloroform:methanol:ammonia (90:9:1) obtain 1-N-[1(S)-ethoxycarbonyl)-5-[2-(6-chloro-3,4-dihydro-1,1-dioxo-7-sulfamoyl-1,2,4-benzothiadiazin-3-yl)acetamido]pentyl]-(S)-alanyl-2(S)-benzyloxycarbonyl-cis,syn-octahydroindole.

E. Combine the product of part D (2.2 g) with 20% hydrogen bromide in acetic acid (50 ml) and stir 4 hours at room temperature (R.T.) Concentrate the resultant mixture, treat with diethyl ether and filter to obtain a crude solid. Chromatograph the resultant solid an AG-50W-X2 resin (hydrogen form), using 3% pyridine as eluant. Lyophilize eluate fractions to obtain a solid, and chromatograph the solid on sephadex, eluting with methanol to obtain the title compound, $[\alpha]_D^{26} = -25.6°$ (ethanol, C=0.5).

EXAMPLE 2

1-{N-[1(S)-Carboxy-5-[2-(6-chloro-3,4-dihydro-1-1-dioxo-7-sulfamoyl-1,2,4-benzothiadiazin-3-yl)acetamido]pentyl]-(S)-alanyl}-cis,syn-octahydroindole-2(S)-carboxylic acid Combine the product of part D of Example 1 (1.8 g) with 1N NaOH (10.8 ml) and allow to stand 16 hours. Add 1N HCl (10.8 ml) to the resultant solution and filter the solid which precipitates to obtain the title compound, m.p. 205°–209° C.

EXAMPLE 3

1-{N-[1(S)-Ethoxycarbonyl-4-[2-(6-chloro-3,4-dihydro-1,1-dioxo-7-sulfamoyl-1,2,4-benzothiadiazin-3-yl)acetamido]butyl]-(S)-alanyl}-cis,syn-octahydroindole-2(S)-carboxylic acid, hydrochloride A. Dissolve N-carbobenzyloxy-(S)-ornithine, ethyl ester (49.5 g) t-butyl α-bromopropionate (75 g) and triethylamine (75 ml) in DMF (400 ml), and heat this solution at 80° for 18 hours. Cool the reaction mixture, add water (2000 ml) and extract with ether (4×400 ml). Dry the organic layer over MgSO4 and concentrate the dried ether solution in vacuo. Chromatography the resultant residue (20 g portions) on Waters Prep 500 using 4 cartridges and hexane:EtOAc (3:1) as eluant to give N-[1(S)-ethoxycarbonyl-4-(benzyloxy-carbonylamino)butyl]-(S)-alanine, t-butyl ester and the corresponding (R)-alanine isomer.

B. Dissolve the product of step A (23.32 g) in absolute ethanol (200 ml) and water (200 ml). Add 10% palladium on charcoal (7.0 g). Hydrogenate at 50 psi for 3 hours. Filter and concentrate in vacuo to give N-[1(S)-ethoxycarbonyl-4-aminobutyl]-(S)-alanine, t-butyl ester (use immediately in next step).

C. Dissolve the product of step B (15.23 g), 3-carboxymethyl-6-chloro-3,4-dihydro-7-sulfamoyl-1,2,4-benzothiadiazine-1,1-dioxide (19.6 g), DCI (10.83 g) and 1-hydroxybenzotriazole (8.45 g) in DMF (150 ml) and stir at room temperature for 18 hours. Concentrate the reaction mixture at room temperature, add dichloromethane and concentrate. Partition the resultant residue between EtOAc and 1N NaHCO3. Dry the organic layer on MgSO4 and concentrate in vacuo. Chromatograph the resultant residue on silica gel (2 cartridges) using EtOAc as eluant on the Waters Prep 500 to give N-1(S)-ethoxycarbonyl-4-[2-(6-chloro-3,4-dihydro-1,1-dioxo-7-sulfamoyl-1,2,4-benzothiadiazin-3-yl)acetamido]butyl-(S)-alanine,t-butyl ester.

D. Treat the product of step C (11.0 g) with dioxane saturated with HCl gas (100 ml) and stir at room temperature for 18 hours. Concentrate in vacuo and triturate and residue with ether to give N-1(S)-ethoxycarbonyl-4-[2-(6-chloro-3,4-dihydro-1,1-dioxo-7-sulfamoyl-1,2,4-benzothiadiazin-3-yl)acetamido]butyl-(S)-alanine hydrochloride.

E. Treat the product of step D (6.26 g) with cis,syn-octahydroindole-2(S)-carboxylic acid benzyl ester (2.15 g), N-methylmorpholine (1.86 ml), 1-hydroxybenzotriazole (1.30 g) and DCI (2.49 g) in DMF (12 ml) at room temperature for 18 hours. Concentrate the resultant mixture in vacuo at room temperature. Add water and extract with EtOAc. Concentrate the dried (MgSO4) organic solution in vacuo at room temperature. Chromatograph the resultant residue on silica gel (1 kg. 60–200 mesh) using EtOAc:absEtOH (9:1) as eluant to obtain 1-[1(S)-ethoxycarbonyl-4-[2-(6-chloro-3,4-dihydro-1,1-dioxo-7-sulfamoyl-1,2,4-benzothiadiazin-3-yl)acetamido]-butyl]-(S)-alanyl-cis,syn-octahydroindole-2(S)-carboxylic acid, benzyl ester.

F. To the benzyl ester of step E, add cold 20% HBr in glacial acetic acid (20 ml), warm to room temperature and stir for 5 hours. Concentrate the reaction mixture in vacuo and triturate the residue with ether to give the corresponding hydrobromide salt.

G. Absorb the product of step F (0.70 g) on a strongly acidic ion exchange column (Bio-Rad AG 50W-X2) and elute with abs, EtOH:H2O (1:4) and then with abs EtOH:H2O:pyridine (77:19:4). Concentrate the desired fractions as determined by thin layer chromatography (desired product is positive to iodine). Obtain the HCl salt by adding the resultant residue to dichloromethane containing HCl gas and concentrate the resulting mixture. Chromatograph the resultant residue (20 g) on a sephadex column (170 g) using methanol as eluant to give the title compound, a white solid $[\alpha]_D^{26} -23.2°$ (MeOH).

EXAMPLE 4

1-{N-[1(S)-carboxy-4-[2-(6-chloro-3,4-dihydro-1,1-dioxo-7-sulfamoyl-1,2,4-benzothiadiazin-3-yl)acetamido]butyl]-(S)-alanyl}-cis,syn-octahydroindole-2(S)-carboxylic acid hydrochloride To the product from Example 3 step F (0.76 g) at 0.5°, add 0.5N NaOH (15 ml), warm to room temperature (½ hour) and stir at room temperature for 18 hours. Concentrate the reaction mixture in vacuo. Treat the resultant residue in the manner described in Example 3, step G to obtain the title compound, $[\alpha]_D^{26} = -16.6°$ (MeOH).

EXAMPLE 5

1-{N-[1(S)-Ethoxycarbonyl-2-(N-(6-chloro-3,4-dihydro-1,1-dioxo-7-sulfamoyl-1,2,4-benzothiadiazin-3-yl-methyl)-carbamoyl)ethyl]-(S)-alanyl}-cis,syn-octahydroindole-2(S)-carboxylic acid A. Combine 3-aminomethyl-6-chloro-7-sulfamoyl-3,4-dihydro-benzothiadiazine-1,1-dioxide hydrochloride (1.09 g), triethylamine (0.31 g), hydroxybenzotriazole hydrate (0.46 g), and N-(t-butoxycarbonyl)-(S)-aspartic acid, α-ethyl ester in dry DMF (20 ml). Add DCI (0.64 g) and stir 1.5 hours. Partition the resultant mixture between water and EtOAc. Wash the organic layer with water, 1.0N NaHCO3, then brine. Dry the organic layer over MgSO4 and concentrate. Crystallize the resultant residue from CHCl3—CH3OH to obtain N-(t-butoxycarbonyl-(S)-aspartic acid, α-ethyl ester, β-(6-chloro-7-sulfamoyl-3,4-dihydro-1,1-dioxo-1,2,4-benzothiadiazine-3-methylamide), m.p. 173° (dec).

B. Combine the product of step A (1.14 g) with 6M HCl/dioxane (10 ml). Stir 15 minutes, decant the solution, and stir the residue with ether. Filter to obtain (S)-aspartic acid, α-ethyl ester, β-(6-chloro-7-sulfamoyl-3,4-dihydro-1,1-dioxo-1,2,4-benzothiadiazine-3-methylamide)hydrochloride.

C. To the product of step B (0.91 g) and triethylamie (0.26 g) in EtOAc (20), add a solution of t-butyl 2R-(trifluoromethanesulfonyloxy)propionate (0.71 g) in EtOAc (5 ml). Stir 3 hours and wash with water, 5% citric acid, 5% NaHCO3, then brine. Dry the organic layer over MgSO4 and concentrate. Chromatograph the resultant residue on silica gel eluting with 1% MeOH-/EtOAc to obtain N-(1(S)-t-butoxycarbonylethyl)-(S)-aspartic aspartic acid, α-ethyl ester, β-(6-chloro-7-sulfamoyl-3,4-dihydro-1,1-dioxo-1,2,4-benzothiadiazine-3-methylamide), $[\alpha]_D^{26} = -19.4°$ (EtOH, C=0.5).

D. Combine the product of step C (0.90 g) with 10 ml 6M HCl/dioxene and anisole (1.6 g). Let stand 24 hours and decant the solution. Triturate with ether and filter to obtain N-(1(S)-carboxyethyl)-(S)-aspartic acid, α-ethyl ester, β-(6-chloro-7-sulfamoyl-3,4-dihydro-1,1-dioxo-1,2,4-benzothiadiazine-3-methylamide)hydrochloride.

E. To the product of step D (0.58 g), triethylamine (0.20 g), hydroxybenzotriazole hydrate (0.15 g) and benzyl (S),(S),(S)-perhydroindole-2-carboxylate (0.26 g) in dry DMF (10 ml), add DCI (0.19 g). After 2 hours, concentrate and partition between EtOAc and 1N NaHCO3. Wash with water, then brine. Dry the organic layer over MgSO4 and concentrate. Chromatograph the resulting residue on silica gel with EtOAc to obtain two isomers of benzyl 1-{N-[1(S)-ethoxycarbonyl-2-(N-(6-chloro-3,4-dihydro-1,1-dioxo-7-sulfamoyl-1,2,4-benzothiadiazin-3-yl-methyl)crbamoyl)ethyl]-(S)-alanyl}cis,syn-octahydroindole-2(S)-carboxylate, (less polar isomer A, $[\alpha]_D^{26} = +4.1°$, more polar isomer B, $[\alpha]_D^{26} = -82.2.°$).

F. Hydrogenate separately each isomer (0.4 g) prepared in Step E in ethanol (70 ml) with 0.4 g 10% Pd/C at 1 atm. until uptake of 0.5 mmole hydrogen. Filter and concentrate the filtrate to obtain the title compound as a solid. Isomer A, $[\alpha]_D^{26} = +28.4°$ (ethanol, c=1). Isomer B, $[\alpha]_D^{26} = -69.3°$ (ethanol, c=1).

EXAMPLE 6

1-{N-[1(S)-Carboxy-2-(N-(6-chloro-3,4-dihydro-1,1-dioxo-7-sulfamoyl-1,2,4-benzothiadiazin-3-YL-methyl)-carbamoyl)ethyl]-(S)-alanyl}-cis,syn-octahydroindole-2(S)-carboxylic acid Following the procedure of Example 4, convert each isomer (A and B) of the product of Example 5 to the corresponding isomer of the title compound. Isomer A, $[\alpha]_D^{26} = -12.7°$. Isomer B, $[\alpha]_D^{26} = -20.0°$.

EXAMPLE 7

1-{N-[1(S)-Ethoxycarbonyl-5-(N-(6-chloro-3,4-dihydro-1,1-dioxo-7-sulfamoyl-1,2,4-benzothiadiazin-2-yl)acetamido)-pentyl]-S-alanyl}-cis,syn-octahydroindole-2(S)-carboxylic acid A. To 6-chloro-3,4-dihydro-1,1-dioxo-7-sulfamoyl-1,2,4-benzothiadiazine (6.0 g) in dry DMF (50 ml). Add Cs2CO3 (3.26 g=10 mmol) and benzyl bromoacetate (4.58 g) and stir 18 hours. Pour into water, extract with ethyl acetate, and wash with water. Dry the organic layer over MgSO4 and concentrate. Chromatograph the resultant residue on silica gel with 10:1 CHCl3—MeOH to obtain benzyl(6-chloro-3,4-dihydro-1,1-dioxo-7-sulfamoyl-1,2,4-benzothiazin-2-yl)acetate.

B. Combine the product of step A (0.44 g) with 0.07 g 10% Pd/C in THF (50 ml). Hydrogenate at 1 atm until uptake of 1.0 eq. hydrogen. Filter and concentrate the filtrate to obtain (6-chloro-3,4-dihydro-1,1-dioxo-7-sulfamoyl-1,2,4-benzothiadiazin-2-yl)acetaic acid as a foam.

C. Treat the product of step B in a manner similar to that described in Example 1, step B to obtain the corresponding 1,2,4-benzothiadiazin-2-acetamide.

D. Treat the product of step C in a manner similar to that described in Example 1, step C to obtain the corresponding hydrochloride.

E. Treat the product of step D in a manner similar to that described in Example 1, step D to obtain 1-{N-[1(S)-ethoxycarbonyl)-5-[N-(6-chloro-3,4-dihydro-1,1-dioxo-7-sulfamoyl-1,2,4-benzothiadiazin-2-yl)acetamido]pentyl]-(S)-alanyl}-2(S)-benzyloxycarbonyl-cis,syn-octahydroindole. F. Treat the product of step E with HBr as described in Example 1 step E to obtain the title compound.

EXAMPLE 8

1-{N-[1(S)-ethoxycarbonyl-2-(N-2-(6-chloro-3,4-dihydro-1,1-dioxo-7-sulfamoyl-1,2,4-benzothiazin-2-yl)ethyl)carbamoyl-ethyl]-(S)-alanyl}-cis,syn-octahydroindole-2S-carboxylic acid A. Treat 6-chloro-3,4-dihydro-1,1-dioxo-7-sulfamoyl-1,2,4-benzothiadiazine with Cs2CO3 and substitute 1,2-dibromoethane for benzylbromoacetate in the procedure of Example 7, step A to obtain 2-(2-bromoethyl)-6-chloro-3,4-dihydro-1,1-dioxo-7-sulfamoyl-1,2,4-benzothiadiazine.

B. Combine the product of step A (12.2 g) with sodium azide (3.9 g) in DMF (200 ml). Stirr 44 hours, extract with ethyl acetate, wash with water, dry the organic layer over MgSO4 and concentrate. Dissolve the resultant residue in ethanol (150 ml), add 5.0 g 10% Pd/C and hydrogenate at 3 atm for 4 hours. Filter and concentrate the filtrate to obtain 2-(2-aminoethyl)-6-chloro-3,4-dihydro-1,1-dioxo-7-sulfamoyl-1,2,4-benzothiadiazine.

C. Treat the product of step B with N-(t-butoxycarbonyl)-(S)-aspartic acid, α-ethyl ester as described in Example 5, step A, and continue the procedure described in Example 5, steps B through F to obtain the title compound.

Using the methods described above and substituting appropriate reagents, the compounds described in the following tables are prepared.

TABLE 1

FORMULA I

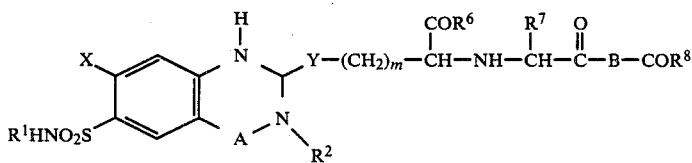

| A | B | p | q | n | Y | X | R¹ | R² | R⁶ | R⁷ | R⁸ | m |
|---|---|---|---|---|---|---|----|----|----|----|----|---|
| SO2 | IIIa | — | — | — | —(CH2)2CONH— | CF3 | CH3 | H | —OCH2CH3 | CH3 | OH | 4 |

TABLE 1-continued
FORMULA I

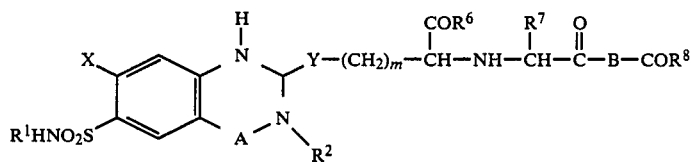

| A | B | p | q | n | Y | X | R¹ | R² | R⁶ | R⁷ | R⁸ | m |
|---|---|---|---|---|---|---|---|---|---|---|---|---|
| SO₂ | IIIc | 1 | 1 | — | —CH₂CON(CH₃)— | Cl | H | CH₃ | OH | H | OH | 3 |
| SO₂ | IIId | 1 | 1 | 0 | —CH₂CONH— | Cl | CH₃ | H | —OCH₂CH₃ | CH₃ | OH | 4 |
| SO₂ | IIIa | — | — | — | —CH₂NHCO— | Cl | H | H | —OCH₃ | CH₃ | OCH₃ | 3 |
| SO₂ | IIIc | 1 | 1 | — | —CH₂—N(CH₃)CO— | CF₃ | H | φ | OH | CH₃ | OH | 4 |
| SO₂ | IIId | 1 | 1 | 0 | —(CH₂)₃NHCO— | Cl | CH₂CH₃ | —CH₂CH₃ | OH | —(CH₂)₄NH₂ | OH | 3 |
| CO | IIIa | — | — | — | —CONH— | Cl | CH₃ | H | —OCH₂CH₃ | CH₃ | OH | 3 |
| CO | IIIb | 0 | 1 | — | —CON(CH₃)— | CF₃ | H | —CH₂φ | OH | —(CH₂)₄NH₂ | OH | 2 |
| CO | IIIc | 0 | 1 | — | —(CH₂)₄CON(φ)— | Cl | CH₃ | CH₃ | OH | CH₃ | OH | 2 |
| CO | IIId | 1 | 1 | 0 | —(CH₂)₂CON(CH₂φ)— | CF₃ | CH₂CH₃ | H | —OCH₂CH₃ | CH₃ | OCH₃ | 4 |
| CO | IIIa | — | — | — | —CH₂NHCO— | Cl | H | —φ | OH | —CH₂CH₃ | OH | 1 |
| CO | IIIb | 0 | 1 | — | —(CH₂)₄N(CH₂φ)CO— | Cl | CH₃ | H | OH | CH₃ | —OCH₂CH₃ | 3 |
| CO | IIIc | 1 | 1 | — | —(CH₂)₂NφCO— | CF₃ | CH₃ | CH₃ | —OCH₂CH₃ | —(CH₂)₃NH₂ | OH | 4 |
| CO | IIId | 1 | 1 | 0 | —(CH₂)N(CH₃)CO— | Cl | CH₃ | CH₃ | OH | H | OH | 1 |
| SO₂ | IIIb | 1 | 0 | — | —CH₂CONH— | Cl | H | H | OH | CH₃ | OH | 1 |
| SO₂ | IIIb | 1 | 1 | — | —CH₂N(φ)CO— | Cl | CH₃ | CH₃ | —OCH₂CH₃ | CH₃ | OH | 4 |
| CO | IIIb | 2 | 0 | — | —(CH₂)₂CON(CH₃)— | CF₃ | H | H | OH | CH₃ | OH | 3 |
| CO | IIIb | 0 | 2 | — | —(CH₂)₆NHCO— | Cl | CH₃ | CH₃ | OH | H | OH | 1 |
| SO₂ | IIIc | 1 | 0 | — | —(CH₂)₃CON(CH₂φ)— | Cl | H | CH₃ | OH | CH₃ | OH | 3 |
| SO₂ | IIIc | 1 | 1 | — | —CH₂N(CH₃)CO— | CF₃ | CH₃ | H | —OCH₂CH₃ | —(CH₂)₄NH₂ | OH | 4 |
| CO | IIIc | 2 | 0 | — | —CONH— | Cl | CH₃ | CH₃ | OH | CH₃ | OH | 3 |
| CO | IIIc | 0 | 2 | — | —(CH₂)₄N(CH₃)CO— | Cl | H | H | OH | H | OH | 2 |
| SO₂ | IIId | 1 | 0 | 0 | —(CH₂)₆CON(CH₂φ)— | Cl | CH₃ | —CH₂φ | OH | CH₃ | OH | 4 |
| SO₂ | IIId | 1 | 0 | 1 | —CH₂NHCO— | Cl | H | H | OH | H | OH | 1 |
| CO | IIId | 2 | 0 | 0 | —CH₂NHCO— | CL | H | H | —OCH₃ | CH₃ | OH | 3 |
| CO | IIId | 2 | 0 | 1 | —CONH— | Cl | H | H | OH | —CH₂CH₃ | OH | 4 |

TABLE 2

FORMULA II

R¹HNO₂S—[benzene ring with X]—NH—A—N(R³)(R⁴)—Z—(CH₂)ₘ—CH(COR⁶)—NH—CH(R⁷)—C(=O)—B—COR⁸

| A | B | p | q | n | Z | X | R¹ | R³, R⁴ | R⁶ | R⁷ | R⁸ | m |
|---|---|---|---|---|---|---|---|---|---|---|---|---|
| SO₂ | IIIa | 1 | — | — | —(CH₂)₂CON(CH₃)— | Cl | CH₃ | H, CH₃ | OH | CH₃ | OH | 3 |
| SO₂ | IIIc | 1 | 1 | — | —CH₂CON(φ)— | Cl | H | CH₃, CH₃ | —OCH₂CH₃ | H | OCH₂CH₃ | 4 |
| SO₂ | IIId | 1 | — | 0 | —(CH₂)₆CON(CH₃φ)— | Cl | —CH₂CH₃ | H, φ | OCH₃ | —(CH₃)₄NH₂ | OH | 2 |
| SO₂ | IIIa | 1 | — | — | —(CH₂)₂N(CH₂CH₃)CO— | CF₃ | H | H, —CH₂φ | OH | CH₃ | OCH₂CH₃ | 4 |
| SO₂ | IIIc | 1 | — | — | —(CH₂)₂NφCO— | Cl | H | H, H | —OCH₂CH₃ | —CH₂CH₃ | OH | 1 |
| SO₂ | IIId | 1 | — | 0 | —(CH₂)₃N(CH₂CH₂φ)CO— | Cl | CH₃ | H, H | OH | CH₃ | OCH₂CH₃ | 4 |
| CO | IIIa | — | — | — | —(CH₂)₂NHCO— | Cl | CH₃ | —(CH₂)₄— | OH | CH₃ | OH | 4 |
| CO | IIIb | 0 | — | — | —(CH₂)₃N(φ)CO— | Cl | CH₂CH₃ | H, H | OH | H | OH | 3 |
| CO | IIIc | 0 | 1 | — | —(CH₂)₂N(CH₂φ)CO— | CF₃ | H | H, CH₃ | —OCH₂CH₃ | —(CH₂)₄NH₂ | OCH₃ | 2 |
| CO | IIId | 1 | — | 0 | —(CH₂)₆N(CH₂CH₃)CO— | Cl | CH₃ | —(CH₂)₄ | OH | CH₃ | OH | 1 |
| CO | IIIa | — | — | — | —(CH₂)₂CONH— | CF₃ | H | H, CH₃ | OCH₃ | H | OCH₃ | 4 |
| CO | IIIb | 0 | — | — | —CH₂CONφ— | Cl | CH₃ | H, —CH₂CH₃ | OH | CH₃ | OH | 2 |
| CO | IIIc | 0 | 1 | — | —(CH₂)₅CON(CH₂φ)— | Cl | CH₃ | —(CH₂)₆— | —OCH₂CH₃ | H | OCH₃ | 3 |
| CO | IIId | 1 | — | 0 | —(CH₂)₃CON(CH₂CH₂CH₃)— | Cl | H | H, —CH₂CH₃ | OH | CH₃ | OH | 4 |
| SO₂ | IIIb | 1 | — | — | —CH₂CON(CH₂φ)— | Cl | CH₃ | —CH₂CH₃, —CH₂CH₃ | OH | CH₃ | OH | 3 |
| SO₂ | IIIb | 1 | — | — | —(CH₂)₂NHCO— | CF₃ | —CH₂CH₃ | H, —CH₂φ | OH | H | OH | 2 |
| CO | IIIb | 2 | 0 | — | —(CH₂)₆CON(CH₂CH₃)— | Cl | H | —(CH₂)₅— | OH | —(CH₂)₄NH₂ | OH | 4 |
| CO | IIIb | 0 | 2 | — | —(CH₂)₃N(CH₃)CO— | CF₃ | H | H, H | OH | CH₃ | OH | 1 |
| SO₂ | IIIc | 1 | 0 | — | —CH₂CONH— | Cl | CH₃ | CH₃, CH₃ | OH | CH₃ | OH | 4 |
| SO₂ | IIIc | 1 | 1 | — | —(CH₂)₃N(CH₃)CO— | Cl | CH₃ | H, φ | OH | H | —OCH₂CH₃ | 3 |
| CO | IIIc | 2 | 0 | — | —(CH₂)₃CON(CH₃)— | Cl | H | —(CH₂)₄— | OH | CH₃ | OH | 2 |
| CO | IIIc | 2 | 1 | — | —(CH₂)₂N(φ)CO— | CF₃ | CH₃ | H, H | OH | CH₃ | OH | 4 |
| SO₂ | IIId | 1 | — | 0 | —CH₂CON(CH₃)— | Cl | H | H, H | OH | H | OH | 3 |
| CO | IIId | 1 | — | 1 | —(CH₂)₃NHCO— | Cl | CH₃ | —CH₂CH₃, —CH₂CH₃ | OH | CH₃ | —OCH₂CH₃ | 2 |
| SO₂ | IIId | 2 | — | 0 | —(CH₂)₃CONH— | Cl | H | H, —CH₂φ | —OCH₂CH₃ | —(CH₂)₄NH₂ | OH | 3 |
| CO | IIId | 2 | — | 0 | —(CH₂)₃NHCO— | Cl | H | H, H | OH | CH₃ | OH | 1 |

The following are non-limiting examples of topical ophthalmic formulations for use in the present invention. The term "Compound A" refers to 1-{N-[1(S)-carboxy-5-[2-(6-chloro-3,4-dihydro-1,1-dioxo-7-sulfamoyl-1,2,4-benzothiadiazin-3-yl)acetamido]pentyl]-(S)-alanyl}-cis,syn-octahydro-1H-indole-2(S)-carboxylic acid. It is contemplated, however, that this compound may be replaced by equally effective quantities of other compounds within the scope of formulae I or II as defined above.

EXAMPLE 9

| Topical Solution: | |
|---|---|
| Ingredients | mg/ml |
| Compound A | 10.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1.0 mL. |
| 1.0 N NaOH | q.s. ad pH 7.4 |

Mix the ingredients under sterile conditions and using standard techniques to obtain the ophthamological solution.

EXAMPLE 10

| Topical Solution: | |
|---|---|
| Ingredients | mg/ml |
| Compound A | 0.01 |
| Timolol | 1.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1.0 mL. |
| 1.0 N NaOH | q.s. ad pH 7.4 |

Mix the ingredients under sterile conditions and using standard techniques to obtain the ophthamological solution.

Again, other compounds of formulas I or II could be substituted as well as other beta blockers, such as labetalol, dilevalol, or betaxolol, with the amount of the particular drug varying depending upon the IOP reducing activity of the drugs employed.

EXAMPLE 11

| Topical Solution: | |
|---|---|
| Ingredients | mg/ml |
| Compound A | 0.01 |
| Dexamethasone Sodium Phosphate | 1.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1 mL. |
| 1.0 N NaOH | q.s. ad pH 7.4 |

Mix the ingredients under sterile conditions and using standard techniques to obtain the ophthamological solution.

Again, other compounds of formula I or II and steroidal anti-inflammatory agents such as hydrocortisone, prednisolone, betamethasone, beclomethasone, medrysone, or fluoromethalone can be employed in place of those listed in the formulation above, with the particular amounts varying depending on the drugs employed.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method for controlling elevated intraocular pressure in a mammal which comprises topically administering to an eye of said mammal a composition comprising an intraocular pressure reducing effective amount of a compound represented by the formulae:

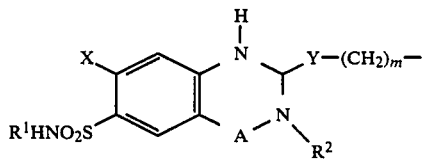

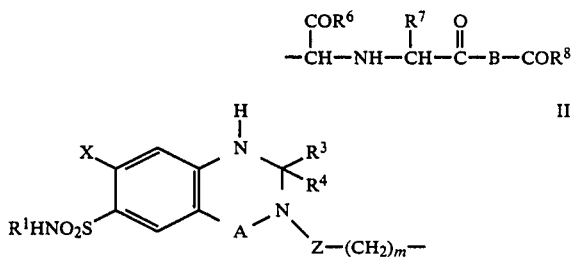

or their isomers or pharmaceutically acceptable salts thereof, in combination with an ophthamologically acceptable carrier for topical use, wherein A is or

X is Cl or $CF_3$;

Y is

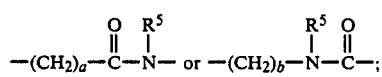

Z is

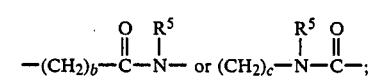

B is

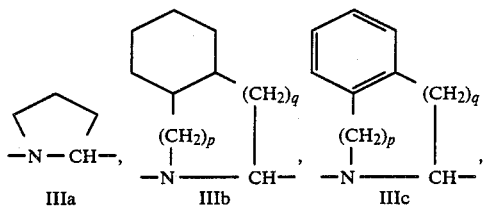

IIIa, IIIb, IIIc

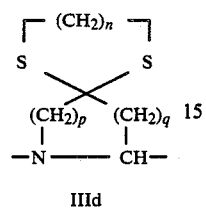

IIId $R^1$ is hydrogen or lower alkyl;

$R^2$ and $R^5$ are independently hydrogen, lower alkyl, phenyl, or phenyl(lower)alkyl;

$R^3$ and $R^4$ are independently hydrogen, lower alkyl, haloloweralkyl, phenyl, or phenyl(lower)alkyl, or $R^3$ and $R^4$ taken together with the carbon to which they are attached can form a 5–7 membered cycloalkyl ring;

$R^6$ and $R^8$ are independently hydroxy, alkoxy having from 1 to 8 carbon atoms, L—$Q_r$—$(CH_2)_s$—O—, wherein L is phenyl, substituted phenyl, 1-naphthyl or 2-naphthyl; Q is oxygen or sulfur; r is 0 or 1 and s is 0 to 4; and wherein the substituents on the phenyl are chosen from group M, wherein M is halogen, hydroxy, trifluoromethyl, alkoxy having from 1 to 6 carbon atoms, alkyl from 1 to 6 carbon atoms, 2-furanyl, 3-furanyl, 2-thienyl, 3-thienyl and phenyl (which phenyl group may be substituted with halogen, hydroxy, trifluoromethyl, alkoxy having from 1 to 6 carbon atoms or alkyl having from 1 to 6 carbon atoms); provided that when s is zero, r is zero; —OCH$_2$—OCO-alkyl wherein the alkyl has from 3 to 8 carbon atoms, —OCH$_2$CO-phenyl, wherein the phenyl may be substituted with group M, 1-gylceryl,

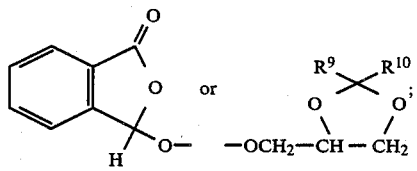

$R^7$ is hydrogen, lower alkyl, or aminoloweralkyl;

$R^9$ is hydrogen, lower alkyl, unsubstituted or substituted phenyl, and substituted or unsubstituted phenyl lower alkyl, wherein phenyl may be substituted by group M;

$R^{10}$ is hydrogen or lower alkyl;

a is 0–8;
b is 1–8;
c is 2–8;
m is 1–4;
n is 0 or 1;
p and q are each 0, 1 or 2, provided that in formulae IIIb and IIIc the sum of p and q is 1 or 2, and that in formulae IIId, p is not 0.

2. A method according to claim 1 wherein $R^6$ and $R^8$ are both hydroxy.

3. A method according to claim 1 wherein B is represented by formula IIIa.

4. A method according to claim 1 wherein B is represented by formula IIIb.

5. A method according to claim 4 wherein p is 0 and q is 1.

6. A method according to claim 1 wherein B is represented by formula IIIc.

7. A method according to claim 6 wherein p and q are each 1.

8. A method according to claim 1 wherein B is represented by formula IIId.

9. A method according to claim 8 wherein p and q are each 1 and n is zero.

10. A topical ophthalmological composition useful for controlling elevated intraocular pressure which comprises an intraocular pressure reducing effective amount of a compound of formulae:

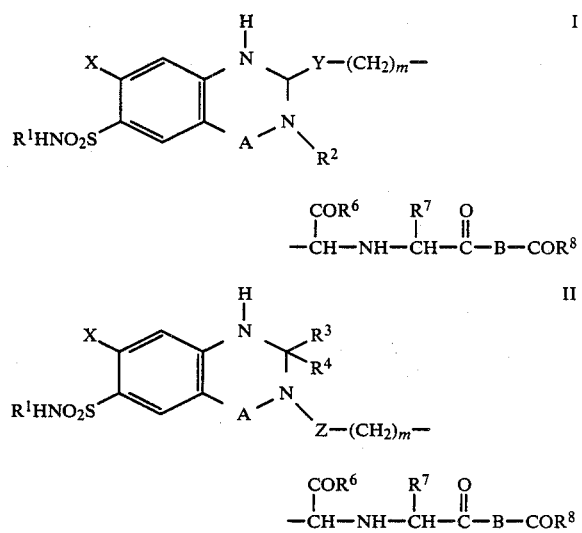

or their isomers or pharmaceutically acceptable salts thereof, in combination with an ophthamologically acceptable carrier for topical use, wherein A is

X is Cl or CF$_3$;

Y is

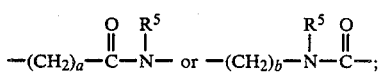

Z is

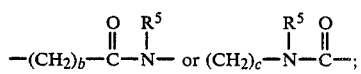

B is

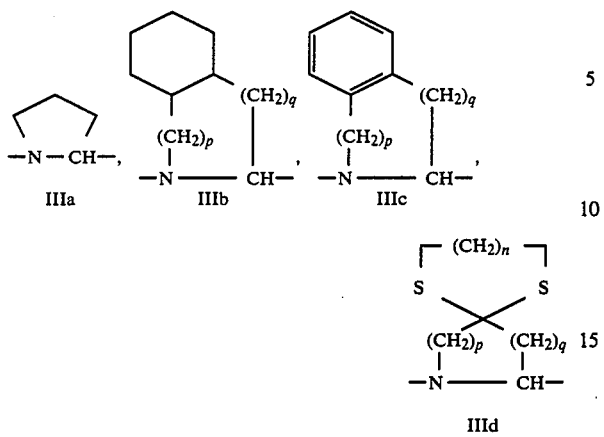

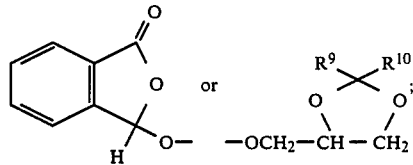

R[1] is hydrogen or lower alkyl;

R[2] and R[5] are independently hydrogen, lower alkyl, phenyl, or phenyl(lower)alkyl;

R[3] and R[4] are independently hydrogen, lower alkyl, haloloweralkyl, phenyl, or phenyl(lower)alkyl, or R[3] and R[4] taken together with the carbon to which they are attached can form a 5–7 membered cycloalkyl ring;

R[6] and R[8] are independently hydroxy, alkoxy having from 1 to 8 carbon atoms, $L-Q_r-(CH_2)_s-O-$, wherein L is phenyl, substituted phenyl, 1-naphthyl or 2-naphthyl; Q is oxygen or sulfur; r is 0 or 1 and s is 0 to 4; and wherein the substituents on the phenyl are chosen from group M, wherein M is halogen, hydroxy, trifluoromethyl, alkoxy having from 1 to 6 carbon atoms, alkyl from 1 to 6 carbon atoms, 2-furanyl, 3-furanyl, 2-thienyl, 3-thienyl and phenyl (which phenyl group may be substituted with halogen, hydroxy, trifluoromethyl, alkoxy having from 1 to 6 carbon atoms or alkyl having from 1 to 6 carbon atoms); provided than when s is zero, r is zero; —OCH₂—OCO—alkyl wherein the alkyl has from 3 to 8 carbon atoms, —OCH₂CO-phenyl, wherein the phenyl may be substituted with group M, 1-glyceryl, R[7] is hydrogen, lower alkyl, or aminoloweralkyl;

R[9] is hydrogen, lower alkyl, unsubstituted or substituted phenyl, and unsubstituted or unsubstituted phenyl lower alkyl, wherein phenyl may be substituted by group M;

R[10] is hydrogen or lower alkyl;

a is 0–8;

b is 1–8;

c is 2–8;

m is 1–4;

n is 0 or 1;

p and q are each 0, 1 or 2, provided that in formulae IIIb and IIIc the sum of p and q is 1 or 2, and that the formulae IIId, p is not 0.

11. The composition according to claim 10 wherein R[6] and R[8] are both hydroxy.

12. The composition according to claim 10 wherein B is represented by formula IIIa.

13. The composition according to claim 10 wherein B is represented by formula IIIb.

14. The composition according to claim 13 wherein p is 0 and q is 1.

15. The composition according to claim 10 wherein B is represented by formula IIIc.

16. The composition according to claim 15 wherein p and q are each 1.

17. The composition according to claim 10 wherein B is represented by formula IIId.

18. The composition according to claim 17 wherein p and q are each 1 and n is zero.

* * * * *